United States Patent
Elango

(10) Patent No.: US 6,555,704 B1
(45) Date of Patent: Apr. 29, 2003

(54) PROCESS FOR THE CARBONYLATION OF ARYLALKYL HALIDES

(75) Inventor: Varadaraj Elango, Corpus Christi, TX (US)

(73) Assignee: BASF Corporation, Mount Olive, NJ (US)

( * ) Notice: Subject to any disclaimer, the term of this patent is extended or adjusted under 35 U.S.C. 154(b) by 0 days.

(21) Appl. No.: 08/445,593

(22) Filed: May 22, 1995

Related U.S. Application Data

(63) Continuation of application No. 07/973,542, filed on Nov. 9, 1992, now abandoned, which is a continuation of application No. 07/834,979, filed on Feb. 14, 1992, now abandoned, which is a continuation of application No. 07/537,865, filed on Jun. 14, 1990, now abandoned, which is a continuation of application No. 07/185,184, filed on Apr. 22, 1988, now abandoned.

(51) Int. Cl.$^7$ .......................... C07C 51/12; C07C 51/14; C07D 487/00; C07D 471/00
(52) U.S. Cl. ........................ 562/406; 546/87; 560/56; 562/466
(58) Field of Search ..................... 546/97; 562/406, 562/466; 560/56

(56) References Cited

U.S. PATENT DOCUMENTS

| | | | |
|---|---|---|---|
| 2,859,253 A | 11/1958 | Snow et al. | 570/195 |
| 4,981,995 A | 1/1991 | Elango et al. | 562/406 |

FOREIGN PATENT DOCUMENTS

| | | |
|---|---|---|
| JP | SHO 44-28699 | 11/1969 |
| JP | Sho 56-35659 | 8/1981 |
| JP | Sho 59-95238 | 6/1984 |
| JP | Sho 59-95239 | 6/1984 |

OTHER PUBLICATIONS

J. March; Advanced Organic Chemistry; *McGraw Hill* (1968) pp. 392–394.

J. March; Advanced Organic Chemistry; *John Wiley & Sons; Third Edition*, pp. 299 and 305.

J. March; Advanced Organic Chemistry; *McGraw–Hill Companyi* (Nov. 1979) p. 501.

Robinson et al.; Stereochemistry of the Dehydration of 1,2–Diphenylpropanols via Iodo Intermediates; *J. Org. Chem.*, (1986) 51, 109–111.

Morrison et al.; Organic Chemistry, *Allyn and Bacon, Inc.*, (1977) pp. 469–471 and 524–525.

Morrison et al.; Study Guide to Organic Chemistry; *Allyn and Bacon, Inc.* (1975).

Elango et al.; Method for producing Ibuprofen; U.S. patent application No. 07/028,514, filed Mar. 20, 1987.

G. Olah; Friedel–crafts and Related Reactions; *Interscience Publishers* (1964) pp. 737–741 and 778.

Sommelet et al.; Chloromethylene Derivatives; *Pharmaceutical, Cosmetics, Perfumes*, p. 1936.

J. Falbe; New Syntheses with Carbon Monoxide; *Springer–Verlag* (1980) p. 250.

Hughes et al.; Reaction Kinetic and the Walden Invertion, Part II. Homogeneous Hydrolysis, Alcoholysis and Ammonolysis of alpha–Phenylethyl Halides; University College, London, (1936) pp. 1201–1208.

Banthorpe et al.; Mechanism of Elimination Reactons. Part II. The Inessentially of Steric Strain in Bimolecular Olefin Elimination; William Ramsay and Ralph Forster Laboratories, University College of London, (1960) pp. 4054–4087.

*Primary Examiner*—Alan L. Rotman
(74) *Attorney, Agent, or Firm*—Kenneth J Meyers, Esq.; Barbara V. Maurer

(57) ABSTRACT

A method is provided for the preparation of alpha-arylpropionic acids such as ibuprofen by carbonylating the corresponding 1-arylethyl halide in an acidic aqueous medium containing a palladium catalyst. In the preparation of ibuprofen, 1-(4'-isobutylphenyl)ethyl halide is reacted with carbon monoxide in an acidic aqueous medium containing a palladium catalyst.

71 Claims, No Drawings

PROCESS FOR THE CARBONYLATION OF ARYLALKYL HALIDES

This is a continuation of application Ser. No. 07/973,542, filed on Nov. 9, 1992, now abandoned; which is a continuation of Ser. No. 07/834,979, filed Feb. 14, 1992, now abandoned; which is a continuation application of Ser. No. 07/537,865, filed on Jun. 14, 1990, now abandoned; which is a continuation of Ser. No. 07/185,184, filed on Apr. 22, 1988, now abandoned.

BACKGROUND OF THE INVENTION

This invention relates to a novel process for the production of alpha-arylpropionic acids. The invention is particularly useful for the production of anti-inflammatory drugs such as 2-(4'-isobutylphenyl)propionic acid, more commonly known as ibuprofen.

Ibuprofen is a well-known non-steroidal anti-inflammatory drug which has been converted from ethical, i.e., prescription, to over-the-counter status. Various processes are known for the production of ibuprofen using 4-isobutylacetophenone as a starting material. Thus, for example, British Patent 971,700 and corresponding U.S. Pat. No. 3,385,886, both assigned to Boots Pure Drug Company, PLC, show the production of phenylalkane derivatives such as ibuprofen in which the first step of the process is the reaction of an alkylbenzene with acetyl chloride in the presence of aluminum chloride to produce an alkylacetophenone which is then subjected to any of various series of subsequent reactions to produce the desired derivative.

Arylpropionic acids have been formed by the carbonylation of the respective arylethyl alcohol. For example, Japanese Kokai Patent No. SHO 55 [1980]-27147, published Feb. 27, 1980 and assigned to Mitsubishi Petrochemical Co., discloses the formation of ibuprofen by reacting 1-(4'-isobutylphenyl)ethanol with carbon monoxide and water in the presence of a hydrogen fluoride catalyst. Japanese Kokai Patent No. SHO 59 [1984]-95238, published Jun. 1, 1984 and assigned to Mitsubishi Petrochemical Co., teaches the formation of alpha-aryl-substituted propionic acids, by reacting an alpha-aryl-substituted ethanol with carbon monoxide and water, alcohol, or phenol, in the presence of a palladium catalyst. An acidic compound such as hydrogen chloride may be added as an auxiliary catalyst and a solvent such as benzene may also be used. The disclosure includes a comparative example in which ibuprofen (not included within the invention) is obtained in very low yield, i.e., 17.1%, when made utilizing the described process. Japanese Kokai Patent No. SHO 59 [1984]-95239, published Jun. 1, 1984 and assigned to Mitsubishi Petrochemical Co., discloses the formation of alpha-(6'-methoxy-2'-naphthyl) propionic acid by reacting alpha-(6'-methoxy-2'-naphthyl) ethanol with carbon monoxide and water in the presence of a palladium catalyst and an acidic compound, e.g., hydrogen chloride. The patent publication also states that if a non-halogen-containing acidic compound is used, it is desirable to add an ionizable metal halide to the reaction.

Japanese Kokai Patent No. SHO 56[1981]-35659, published Sep. 4, 1978 and assigned to Ferrel International Societe Annonim, discloses an anhydrous method of producing a 2-(4'-isobutylphenyl)propionic acid ester by treating 1-(4'-isobutylphenyl)ethanol (IBPE) with carbon monoxide in a solution containing an alkanol and a catalyst such as palladium bis(triphenylphosphine) dichloro complex. The solution may also contain up to 10% of a mineral acid such as hydrogen chloride.

British Patent 1,565,235, assigned to Mitsubishi Petrochemical Co. discloses a process for producing alpha-arylpropionic acids which have an anti-inflammatory, analgesic or antipyretic effect. The process comprises reacting an arylethylene with carbon monoxide under pressure in the presence of a carbonylation catalyst and in the presence of water and/or a lower alcohol to carbonylate the arylethylene into the alpha-arylpropionic acid. The starting materials for the arylethylenes can be prepared such as by the dehydration of arylethyl alcohols or by the dehydrohalogenation of arylethyl halides. The arylethylenes can be purified by means of a single distillation or re-crystallization to obtain the products with a sufficiently high purity to be used as the starting material for the subsequent carbonylation step. An example in the patent describes the dehydrohalogenation of alpha-(4-isobutylphenyl)ethyl chloride to obtain 4-isobutylstyrene and then carbonylating 4-isobutylstyrene in the presence of water, methyl alcohol, hydrogen chloride, and bis(triphenolphosphine)dichloropalladium (II).

In copending, commonly assigned U.S. Ser. No. 158,141, filed Mar. 4, 1988, 2-(4'-isobutylphenyl)propionic acid, i.e., ibuprofen, is prepared by carbonylating 1-(4'-isobutylphenyl)ethanol (IBPE) with carbon monoxide in an acidic aqueous medium at a temperature of at least about 10° C. and a carbon monoxide pressure of at least about 500 psig, and in the presence of 1) a catalyst consisting essentially of a palladium compound in which the palladium is complexed with at least one acid stable, monodentate phosphine ligand freely miscible with the organic phase of the reaction medium; 2) dissociated hydrogen ions from an acid which is substantially completely ionizable in a dilute aqueous solution such that the molar ratio of hydrogen ions to IBPE added to the reaction zone is at least about 0.15 and the mole ratio of hydrogen ions to water is at least 0.026; and 3) dissociated halide ions such that the molar ratio of halide ions to IBPE added to the reaction zone is at least about 0.15.

the process is immediately described above for preparing ibuprofen by carbonylating 1-(4'-isobutylphenyl)ethanol is generally a multi-stage process in which the carbonylation reaction to produce ibuprofen is integrated with a method of producing IBPE from isobutylbenzene. Thus, isobutylbenzene is subjected to Friedel-Crafts reaction with an acetylating agent such as acetic acid, acetic anhydride, acetyl fluoride, acetyl chloride, acetyl bromide, methyl acetate in the presence of the Friedel-Crafts catalyst such as hydrogen fluoride to produce 4'-isobutylacetophenone (IBAP) which is subsequently reduced with hydrogen in the presence of a hydrogenation catalyst or with a reducing agent containing available hydrogen, to obtain IBPE.

An alternative process for producing alpha-aryl-propionic acids from the carbonylation of the respective 1-aryl ethyl alcohols is the carbonylation of secondary benzyl halides to the corresponding carboxylic acid. In such a known process, the secondary benzyl halides are carbonylated in the presence of a carbonylation catalyst in a basic medium. For example, in an article "Cobalt-Catalyzed Synthesis of Alpha-Arylpropionic and Diarylacetic Acids", *Journal of Organometallic Chemistry* 282 (1985) 277–282, there is disclosed the cobalt-catalyzed carbonylation of ArCH(R)X (R=$CH_3$, $C_6H_5$; X=Cl, Br) in alcoholic solvents under atmospheric pressure of CO. It is stated therein that selective, high yield synthesis of the corresponding acids can be achieved within a very narrow range of experimental conditions. Similarly, U.S. Pat. No. 4,536,595 and related European Patent Applications 76,721 and 76,722 disclose forming alpha-arylpropionic acids such as ibuprofen by carbonylating the respective secondary benzyl halides in the presence of a cobalt hydrocarbonyl catalyst and an anhydrous alcoholic solvent. U.S. Pat. Nos. 4,152,352 and 4,351,952 disclose the formation of arylpyruvic acids by reacting an arylmethyl halide with carbon monoxide in the presence of a cobalt carbonyl catalyst and a base. U.S. Pat. No. 3,974,202 discloses producing an alkyl ester of arylacetic acid by reacting the arylmethyl halide with CO and an alcohol in basic reaction medium in the presence of a cobalt catalyst. U.S. Pat. No. 4,713,484 discloses the formation of carboxylic acid salts by carbonylating an organic halide with an alcohol, CO, and a base in the presence of a palladium catalyst and an excess of tertiary phosphine.

The process for carbonylating the arylalkyl halides to carboxylic acids in base medium has several disadvantages. For one, the carboxylic acid salt of an alkali metal is formed instead of the acid. Consequently, the acid has to be obtained in a separate step by acidification of the salt such as with mineral acids. Additionally, reactions on the arylalkyl halides under carbonylation conditions often result in double carbonylation which leads to the formation of pyruvic acids. Several of the patents mentioned above are directly concerned with the formation of pyruvic acids. Additional disadvantages are that the reactions are not selective over a broad range of reaction conditions and, thus, often a narrow range of conditions must be employed to obtain better yields and selectivity of the desired product.

A process for producing alpha-arylpropionic acids, in particular those of special interest to the pharmaceutical industry as anti-inflammatory, analgesical, antipyrethical agents, etc., and which would be free of the disadvantages of the processes of the prior art such as described above, would inevitably find wide usage. The development of such a process is the primary objective of the present invention.

SUMMARY OF THE INVENTION

In accordance with this invention, alpha-arylpropionic acids are prepared by carbonylating the corresponding 1-arylethyl halides in aqueous acidic medium. The invention is useful in the preparation of 2-(4'-isobutylphenyl)propionic acid, i.e., ibuprofen, by carbonylating 1-(4'-isobutylphenyl) ethyl halide with carbon monoxide in an acidic aqueous medium in the presence of a palladium catalyst. Moreover, in the formation of ibuprofen from isobutylbenzene, a two-step process has been developed comprising (1) a haloalkylation reaction in which isobutylbenzene is reacted with a haloalkylating agent such as acetaldehyde with hydrogen chloride to form 1-(4'-isobutylphenyl)ethyl chloride and, (2) a carbonylation in which the 1-(4'-isobutylphenyl)ethyl chloride is carbonylated in aqueous acid medium in the presence of a palladium catalyst to ibuprofen.

DETAILED DESCRIPTION OF THE INVENTION

In its broadest aspect, the present invention is directed to the production of alpha-arylpropionic acids having the formula:

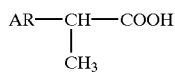

wherein AR represents phenyl or a polynuclear aromatic such as naphthalene and which can be substituted with nonreactive groups including alkyl, cycloalkyl, aryl, halogens, alkoxy, phenoxy, and ketonic. In accordance with this invention, the alpha-aryl-propionic acid is produced by carbonylating the 1-arylethyl halide with carbon monoxide in an acidic aqueous medium and in the presence of a palladium catalyst and dissociated halide ions.

While the process of the present invention can be employed to produce any of the alpha-arylpropionic acids which would be encompassed by above structural formula, the invention is particularly useful in the production of pharmaceutical products. Products of this class, such as for example, 2-(4'-isobutylphenyl)propionic acid, i.e., ibuprofen, and 2-(6'-methoxy-2'-naphthyl)propionic acid, i.e., naproxen, are of special interest to the pharmaceutical industry as anti-inflammatory and analgesical agents.

The carbonylation reaction, in general, proceeds in accordance with equation (I):

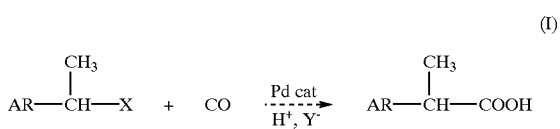

wherein AR represents phenyl or polynuclear aromatic such as naphthalene and which can be substituted with any of the non-reactive substituent groups described above, and X and Y⁻ are the same or different and selected from chlorine, bromine, iodine, or fluorine.

Suitable 1-arylethyl halides include 1-(4'-isobutylphenyl)ethyl chloride, 1-(3'-benzoylphenyl)ethyl chloride, 1-(2'-fluoro-4'-biphenylyl)ethyl chloride, 1-(2'-chloro-4'-biphenylyl)ethyl chloride, 1-(2'-fluorenyl)ethyl chloride, 1-(2'-xanthenyl)ethyl chloride, 1-(5H)-[1]benzopyrano[2,3b]pyridin-7-yl)ethyl chloride, 1-(2'-biphenylenyl)ethyl chloride, 1-(6'-methoxy-2'-naphthyl)ethyl chloride, 1-(4'-methoxyphenyl)ethyl chloride, 1-phenylethyl chloride.

In carrying out the carbonylation reaction, water may be present in an amount, for example, of about 1 to 600%, preferably about 10 to 300%, based on the weight of arylethyl halide initially present; the temperature of reaction may be, for example, in the range of about 10 to 225° C., preferably about 70 to 175° C.; the carbon monoxide pressure may be, for example, in the range of about 100 to 5000 psig, preferably about 600 to 3000 psig; and the total reaction time may be, for example, in the range of about 0.1 to 24 hours, preferably about 1 to 10 hours.

The palladium catalyst employed may or may not be complexed with at least one ligand. Some palladium catalysts which may be used wherein the palladium is complexed with an appropriate ligand are as follows: bis(triphenylphosphine)dichloro complex, bis(tributylphosphine)dichloro complex, bis(tricyclohexylphosphine)dichloro complex, pi-allyltriphenylphosphinedichloro complex, triphenylphosphine-piperidinedichloro complex, bis(cyclohexyloxime)dichloro complex, 1,5,9-cyclododecatrienedichloro complex, bis(triphenylphosphine)dicarbonyl complex, bis(triphenylphosphine)diacetate complex, bis(triphenylphosphine)dinitrate complex, bis(triphenylphosphine)sulfate complex, 2,4-pentanedione complex, tetrakis(triphenylphosphine) complex, and complexes in which some of the ligands are carbon monoxide such as chlorocarbonylbis(triphenylphosphine) complex, all complexes of palladium. Also suitable as a catalyst is palladium metal on a suitable catalyst support such as carbon, alumina, silica, or an inert polymer which can tolerate the conditions of reaction, complexed with one or more of these foregoing ligands. The catalyst complex may be present in an amount such that the mole ratio of palladium to arylethyl halide is in the range, for example, of about 1:25 to 1:20,000, preferably about 1:75 to 1:10,000, and most preferably about 1:100 to 1:6000.

The preferred catalysts are complexes of palladium with phosphine ligands. The palladium salts and phosphine ligands making up the catalyst complexes may also be added separately to the reaction zone. In such a case, the amount of ligand added is preferably sufficient to complex with the palladium present such that the P:Pd mole ratio is equal to at least about 1:1 when the Pd:arylethyl halide mole ratio is at least about 1:5,000. However, when the latter ratio is below 1:10,000, it is necessary to use an excess of phosphine ligand such that the P:Pd ratio is at least about 2:1.

The dissociated hydrogen ions and halide ions may be conveniently added to the reaction as hydrogen halide, e.g., hydrogen chloride, hydrogen bromide, or hydrogen iodide. However, it is also possible to add the hydrogen ions and halide ions from separate sources. For example, other ionizable acids, e.g., inorganic acids, such as sulfuric acid, phosphoric acid or polyphosphoric acid, or organic acids, e.g., sulfonic acids such as p-toluenesulfonic acid, methanesulfonic acid or trifluoroacetic acid, may be used as the source of hydrogen ions. Similarly, other water-soluble and ionizable halide compounds, as for example, halide salts wherein the cation does not interfere with the reaction, e.g., alkali metal halides such as potassium and sodium chlorides, bromides, and iodides may be used as the source of halide ions. The molar ratio of hydrogen ions and halide ions to arylethyl halide each may be in the range, for example, of about 0.1 to 5, preferably about 0.2 to 2.0.

Although not necessary for the operability of the process, in some instances, it may be advantageous to utilize an organic solvent for the reaction. Suitable organic solvents which may be used in the process of this invention are, for example, ketones such as methylethyl ketone, acetone, 2-pentanone, 3-pentanone, and acetophenone, aromatic hydrocarbons such as benzene and toluene, and cyclic ethers such as tetrahydrofuran and dioxane. Ketones and ethers are the preferred solvents. The solvent may be present in a weight ratio of solvent to arylethyl halide in the range, for example, of about 0 to 1000:1, preferably about 0 to 10:1.

An inorganic salt may also be present during the reaction. Inorganic salts which may be used are, for example, those yielding anions comprising oxygen, and sulfur, phosphorus, aluminum or silicon, including such anions as hydrogensulfate, pyrosulfate, ortho-phosphate, pyrophosphate, aluminate, or silicate and cations such as sodium, potassium, calcium, or magnesium, or another cation which does not interfere with the reaction, e.g., ammonium or alkylammonium such as tetrabutylammonium. Other inorganic salts such as calcium chloride may also be added. The inorganic salt, if used, will generally be present at a concentration of, for example, about 0.1 to 50%, preferably about 1 to 2% by weight of total charge.

In addition to those mentioned previously, other additives and ligands may be added to the reaction, e.g., acetophenone and p-mercaptoacetophenone. The latter additives appear to be useful in raising the ratio of ibuprofen to corresponding linear isomer, viz., 3-(4'-isobutylphenyl)propionic acid (3-IPPA), obtained by the method of this invention.

The 1-arylethyl halides employed as the starting materials in the production of the 2-arylpropionic acids can be obtained from any commercial source or formed by any conventional process. For example, the chlorides can be produced by reacting the 1-arylethyl alcohols with hydrogen chloride in the liquid phase in the presence of a metal chloride catalyst such as calcium chloride, sodium chloride, potassium chloride, etc. Known techniques for forming the bromides and iodides may also be used and include the reaction of the respective alcohols with phosphorus tribromide in a basic medium. In the formation of ibuprofen, the alpha-arylethyl halide may be formed by reacting the hydrogen halide with 1-(4'-isobutylphenyl)ethanol (IBPE). Another method of forming the 1-arylethyl halide would be to react vinylbenzenes, e.g., styrene, with a hydrogen halide.

A particularly useful method of obtaining the 1-aryl-ethyl halides is by the haloalkylation of aromatic compounds such as benzene and derivatives thereof. The process is known and disclosed in U.S. Pat. Nos. 2,859,253 and 3,933,326, and is further described in "Freidal-Crafts and Related Reactions", Vol. 2, Part 2, page 659, G. Olah, editor, all of which are herein incorporated by reference. The process involves reacting the aromatic compound with both an alkylating agent and a halide in the presence of a Lewis acid. Effective haloalkylating agents include acetaldehyde, paraldehyde, 1,1-dimethoxyethane, di-(1-chloroethyl)ether with hydrogen chloride, hydrogen bromide or hydrogen iodide. Generally, the mole ratio of the haloalkylating reagent to aromatic compound will range between about 0.5 to 2.5:1 and, preferably from about 1.0 to 1.5:1. Lewis acids which can be employed include $ZnCl_2$, $SnCl_4$, $AlCl_3$, $BF_3$, $FeCl_3$, $TiCl_4$, as well as protic acids such as HCl, HBr, HI, HF, $H_2SO_4$, $H_3PO_4$, $ClSO_3H$, and acetic acid. Molar ratios of Lewis acid to aromatic substance may be from about 1:1 to about 5:1 and, preferably, between about 2 to 3:1. If a gaseous hydrogen halide is used, it can be bubbled at a suitable rate.

The reaction can be carried out with or without a solvent. The reaction may be carried out with excess aromatic compound serving as the solvent or with an inert solvent such as acetic acid, diethyl ether, tetrahydrofuran, dimethyl formamide, carbon tetrachloride, chloroform, methylene chloride, chloroethyl ether, nitrobenzene, and carbon disulfide. The amount of solvent employed is not critical. The temperature of the reaction may range from between about −70 to 150° C. and preferably from about 0 to about 80° C. Reaction time will be between about 1 to about 48 hours and, preferably between 3 to 24 hours.

The haloalkylation of aromatic compounds provides an advantageous route to the formation of ibuprofen from isobutylbenzene. Thus, it is now possible to produce ibuprofen from isobutylbenzene in two steps. The first step would be haloethylation of isobutylbenzene by the method as described above. The 1-arylethyl halide which is formed can then be carbonylated as previously described to ibuprofen.

The following examples are intended to illustrate the invention and are not to be construed so as to limit the invention strictly thereto.

EXAMPLE 1

This example is intended to describe the process for preparing 1-(4'-isobutylphenyl)ethyl chloride from isobutylbenzene.

Isobutylbenzene (402 g, 3 mol) and zinc chloride (136 g, 1 mol) are fed into a one liter flask equipped with termometer, stirrer, and gas inlet tube. The reaction is maintained below 10° C. by external cooling. A mixture of acetaldehyde (44 g, 1 mol) and isobutylbenzene (67 g, 0.5 mol) are added to the flask dropwise for 2 hours while maintaining the temperature of the flask below 10° C. The reaction is heated to room temperature and HCl is passed through the reaction medium in the flask for about 2 hours. The reaction is stirred for 6 hours. The solution is quenched with water and the organic layer is separated from the aqueous layer. The organic layer is washed with sodium bicarbonate and water, and then dried. It is then stripped of isobutylbenzene and vacuum distilled to give 1-(4'-isobutylphenyl)ethyl chloride.

EXAMPLE 2

This is a control example related to the formation of ibuprofen by carbonylating 1-(4'-isobutylphenyl)ethyl chloride. The charge did not include a sufficient amount of hydrochloric acid to meet the disclosed molar quantities of dissociated hydrogen and halide ions needed to yield desired amounts of ibuprofen.

1-(4'-isobutylphenyl)ethyl chloride (3.5 g, 17.8 mmol), $PdCl_2(PPh_3)_2$ (0.70 mg, 0.1 mmol), 5% HCl (1 mL, 1.3 mmol), benzene (80 mL), and acetophenone (0.1 g, 0.8 mmol) were charged to a 300 cc Hastelloy C autoclave which was sealed and purged twice with $N_2$ (50 psi). The autoclave was pressure checked with CO (250 psig) and pressured with CO to 950 psig. The contents were heated to 104° C. and the pressure increased to 1,150 psig. The reactants were stirred for 5 hours. The autoclave was cooled to room temperature, vented of CO and washed with 40 mL of water. The reaction mixture was treated with 40 mL of 2N aqueous NaOH and the organic layer was separated. The organic fraction was dried and concentrated under reduced pressure to give a brown oil product (3.0 g). The sample was anlayzed by gas-liquid chromatography (GLC) and was shown to contain 0.60% of ibuprofen.

The aqueous NaOH layer was acidified with HCl and extracted two times with $CH_2Cl_2$ (60 mL). The $CH_2Cl_2$ layer was concentrated to give 100 mg of a slightly yellow colored liquid which was analyzed by GLC as ibuprofen.

EXAMPLES 3–7

Ibuprofen was formed by carbonylating 1-(4'-isobutylphenyl)ethyl chloride and 1-(4'-isobutylphenyl)ethyl bromide under carbonylating conditions as disclosed in the instant specification. The reactants including the aryl halide, solvent, acid and catalyst as well as the molar amounts thereof are all set forth in Table 1. Product selectivity including ibuprofen and major by-products are also set out in Table 1. The catalyst utilized was $PdCl_2(PPh_3)_2$.

All the reactants were charged to a 300 CC Hastelloy C autoclave which was sealed and purged twice with $N_2$ (50 psig) and twice with CO (200 psig) before being pressured to 800 psig at room temperature with CO. The contents were then heated to reaction temperature and the reaction continued for the time expressed in Table 1 for each example.

After the reaction, the autoclave was cooled to room temperature, vented to CO and the reaction medium recovered. The organic layer was separated from the aqueous layer. The aqueous layer was extracted three times each with 75 mL ethyl acetate. The combined organic layers were dried and concentrated to obtain the product. The product obtained was analyzed by GLC. The analysis is shown in Table 1.

TABLE 1

| Example | Substrate mmol | Solvent/mL | Acid mmol | mol/L | Catalyst mmol | Temp ° C. | Time h | Hal conv wt. % | Selectivity sty wt % | ibu wt % | iso wt. % | poly wt % |
|---|---|---|---|---|---|---|---|---|---|---|---|---|
| 1-(4'-isobutylphenyl)ethyl chloride | | | | | | | | | | | | |
| 3 | 56.0 | MEK/27 | HCl/69, | 2.7 | 0.37 | 125 | 18 | 99 | tr | 70 | 8 | 11 |
| 4 | 56.0 | MEK/27 | HBr/50, | 2.0 | 0.37 | 125 | 7 | 99 | tr | 74 | 5 | 7 |
| 5 | 56.0 | MEK/27 | HBr/50, | 2.0 | 0.37 | 125 | 6 | 99 | tr | 65 | 3 | 4 |
| 6 | 56.0 | MEK/27 | HCl/50, | 2.7 | 0.11 | 110 | 4 | 99 | 1 | 72 | 2 | 3 |
| 1-(4'-isobutylphenyl)ethyl bromide | | | | | | | | | | | | |
| 7 | 56.0 | MEK/27 | HBr/50, | 2.0 | 0.37 | 110 | 6 | 99 | tr | 71 | 13 | 11 |

The abbreviations are: MEK = methylethyl ketone, Hal = 1-(4'-isobutylphenyl)ethyl halide, sty = 4-isobutylstyrene, ibu = ibuprofen, iso = 3-(4'-isobutylphenyl)propionic acid, poly = polymeric heavy ends, tr = trace.
All examples run with 11 mmol of $KHSO_4$ added.

EXAMPLES 8–12

Other aryl halides were carbonylated using the process of the present invention. Reactants, concentrations thereof and operating parameters are set forth in Table 2. Product analysis is also set forth in Table 2. The carbonylation catalyst used was $PdCl_2(PPh_3)_2$. The process was conducted as in Examples 3–7. Product recovery was also conducted in the same manner as described above and the product was analyzed by GLC.

TABLE 2

| Example | Substrate mmol | Solvent/mL | Acid mmol | Acid mol/L | Catalyst mmol | Temp °C | Time h | Hal conv wt. % | Selectivity acid wt % | sty wt % | eth wt. % | poly wt % |
|---|---|---|---|---|---|---|---|---|---|---|---|---|
| 1-chloro-1-phenylethane | | | | | | | | | | | | |
| 8 | 56.0[1] | MEK/27 | HCl/69 | 2.7 | 0.28 | 115 | 6 | 99 | 72 | tr | — | 9 |
| 1-(4'-methoxyphenyl)ethyl chloride | | | | | | | | | | | | |
| 9 | 56.0[2] | MEK/40 | HCl/41 | 2.7 | 0.28 | 105 | 6 | 99 | 43 | — | 9 | 32 |
|  | 56.0 | MEK/35 | HCl/41 | 2.7 | 0.28 | 105 | 6 | 99 | 42 | — | 5 | 42 |
| 1-(6'-methoxy-2'-naphthyl)ethyl chloride | | | | | | | | | | | | |
| 10 | 56.0[2] | MEK/27 | HCl/69 | 2.7 | 0.37 | 125 | 6 | 99 | 25 | 21 | — | — |
| 11 | 56.0 | MEK/50 | HCl/14 | 2.7 | 0.37 | 105 | 6 | 99 | 52 | 5 | 17 | — |

The conversion and selectivity values are reported as relative area percent based on the GLC analysis. The abbreviations are: Hal = 1-arylethyl halide, acid = 2-arylpropionic acid, sty = arylstyrene, eth = 1-arylethane, poly = polymeric heavy ends, tr = trace.
[1] = 2-(phenyl)propionic acid ethyl ester observed (9%).
[2] = addition of 11 mmol of $KHSO_4$.

What is claimed is:

1. A process for preparing ibuprofen from a corresponding halide substrate, which consists essentially of:
   combining an initial reactant consisting of a 1-(4'-isobutylphenyl)ethyl halide with carbon monoxide in an acidic medium containing water, which is present in an amount of about 1% to 600% based on the weight of the halide initial reactant, in the presence of a palladium catalyst, wherein the mole ratio of palladium to 1-(4'-isobutylphenyl)ethyl halide is from about 1:25 to 1:20,000, and wherein said acidic aqueous medium further includes dissociated hydrogen ions and halide ions such that the molar ratios of dissociated hydrogen ions and halide ions to 1-(4'-isobutylphenyl)ethyl halide initial reactant are each about 0.1 to 5, at a temperature in the range of about 10° C. to 225° C., and a carbon monoxide pressure of about 100 to 5,000 psig, to form said ibuprofen; and
   wherein said palladium catalyst includes (a) palladium having a valence of 0–2, and (b) at least one ligand, which can tolerate conditions of reaction and which is complexed with the palladium.

2. A process for preparing ibuprofen from a corresponding halide substrate, which consists essentially of:
   charging a reactor with 1-(4'-isobutylphenyl)ethyl halide; and
   carbonylating said halide with carbon monoxide;
   wherein the carbonylation takes place in an acidic medium containing water, which is present in an amount of about 10% to 300% based on the weight of the halide charged, in the presence of a palladium catalyst, wherein the mole ratio of palladium to 1-(4'-isobutylphenyl)ethyl halide is from about 1:75 to 1:10,000, and wherein said acidic aqueous medium further includes dissociated hydrogen ions and halide ions such that the molar ratios of dissociated hydrogen ions and halide ions to 1-(4'-isobutylphenyl)ethyl halide charged are each about 0.2 to 2, at a temperature in the range of about 70° C. to 175° C. and a carbon monoxide pressure of about 600 to 3,000 psig, to form said ibuprofen; and
   wherein said palladium catalyst includes (a) palladium having a valence of 0–2, and (b) at least one ligand, which can tolerate conditions of reaction and which is complexed with the palladium.

3. A process for preparing ibuprofen from a corresponding halide substrate, which consists essentially of:
   charging a reactor with a 1-(4'-isobutylphenyl)ethyl halide; and
   carbonylating said halide with carbon monoxide;
   wherein the carbonylation takes place in an acidic medium containing methyl ethyl ketone and water, which is present in an amount of about 10% to 300% based on the weight of the halide charged, in the presence of a palladium catalyst, wherein the mole ratio of palladium to 1-(4'-isobutylphenyl)ethyl halide is from about 1:100 to 1:6,000, and wherein said acidic aqueous medium further includes dissociated hydrogen ions and chloride ions such that the molar ratios of dissociated hydrogen ions and chloride ions to 1-(4'-isobutylphenyl)ethyl halide charged are each about 0.2 to 2.0, at a temperature in the range of about 70° C. to 175° C., and a carbon monoxide pressure of about 600 to 3,000 psig, to form said ibuprofen; and
   wherein said palladium catalyst includes (a) palladium having a valence of 0–2, and (b) at least one ligand, which can tolerate conditions of reaction and which is complexed with the palladium.

4. A process for preparing ibuprofen from an ibuprofen substrate, which consists essentially of:
   charging a reactor with said ibuprofen substrate, wherein said ibuprofen substrate consists of 1-(4'-isobutylphenyl)ethyl chloride; and
   carbonylating said substrate with carbon monoxide;
   wherein said carbonylation takes place in an acidic medium containing water, which is present in an amount of about 10% to 300% based on the weight of the chloride charged, in the presence of a palladium catalyst, wherein the mole ratio of palladium to 1-(4'-isobutylphenyl)ethyl chloride is from about 1:100 to 1:6,000, and wherein said acidic aqueous medium further includes dissociated hydrogen ions and chloride ions such that the molar ratios of dissociated hydrogen ions and chloride ions to 1-(4'-isobutyl-phenyl)ethyl chloride charged are each about 0.2 to 2, at a temperature in the range of about 70° C. to 175° C., and a carbon monoxide pressure of about 600 to 3,000 psig, to form said ibuprofen; and
   wherein said palladium catalyst includes (a) palladium having a valence of 0–2, and (b) at least one ligand, which can tolerate conditions of reaction and which is complexed with the palladium.

5. The process of claim 4, wherein the palladium catalyst is selected from the group consisting of palladium bis(triphenylphosphine)dichloro complex, palladium bis(tributylphosphine)dichloro complex, palladium bis(tricyclohexylphosphine)dichloro complex, palladium piallyltriphenylphosphinedichloro complex, palladium triphenylphosphinepiperidinedichloro complex, palladium bis(cyclohexyloxime)dichloro complex, palladium 1,5,9-cyclododecatrienedichloro complex, palladium bis(triphenylphosphine)dicarbonyl complex, palladium bis(triphenylphosphine)diacetate complex, palladium bis(triphenylphosphine)dinitrate complex, palladium bis(triphenylphosphine)sulfate complex, palladium 2,4-pentanedione complex, palladium tetrakis(triphenylphosphine) complex, and palladium chlorocarbonylbis(triphenylphosphine) complex.

6. The process of claim 5, wherein the carbonylation reaction is carried out in the presence of an organic solvent selected from the group consisting of methyl ethyl ketone, acetone, 2-pentanone, 3-pentanone, acetophenone, benzene, toluene, tetrahydrofuran, and dioxane, and wherein the solvent is present in a weight ratio of solvent to the 1-(4'-isobutylphenyl)ethyl chloride of from about 0 to 10:1.

7. A method of preparing ibuprofen comprising:
(A) charging a reactor with 1-(4'-isobutylphenyl)ethyl halide; and
(B) carbonylating the 1-(4'-isobutylphenyl)ethyl halide with carbon monoxide in an acidic aqueous medium in the reactor in the presence of (a) a palladium catalyst in which the palladium has a valence of 0–2, and (b) at least one ligand, which can tolerate conditions of reaction, complexed with the palladium.

8. The method of claim 7, wherein said palladium catalyst comprises a palladium compound complexed with at least one ligand selected from the group consisting of trivalent phosphorus compounds, carbonyl compounds, compounds containing pi-allyl groups, amines, oximes, and olefins.

9. The method of claim 7, wherein said ligand is a tri(organo)phosphine.

10. The method of claim 7, wherein said ligand is triphenylphosphine.

11. The method of claim 10, wherein said catalyst is a palladium bis(triphenylphosphine)dichloro complex.

12. The method of claim 7, wherein said acidic aqueous medium further includes dissociated hydrogen and halide ions.

13. The method of claim 12, wherein the source of said hydrogen ions and halide ions is a hydrogen halide.

14. The method of claim 13, wherein said hydrogen halide is hydrogen chloride.

15. The method of claim 13, wherein said hydrogen halide is hydrogen bromide.

16. The method of claim 12, wherein the molar ratio of each of said dissociated hydrogen ions and halide ions to moles of said 1-(4'-isobutylphenyl)ethyl halide is in the range of from about 0.1 to 5.

17. The method of claim 12, wherein the molar ratio of each of said dissociated hydrogen ions and halide ions to moles of said 1-(4'-isobutylphenyl)ethyl halide is from about 0.2 to 2.0.

18. The method of claim 7, wherein said acidic aqueous medium further includes an organic solvent.

19. The method of claim 7, wherein the 1-(4'-isobutylphenyl)ethyl halide is 1-(4'-isobutylphenyl)ethyl chloride.

20. The method of claim 17, wherein the 1-(4'-isobutylphenyl)ethyl halide is 1-(4'-isobutylphenyl)ethyl bromide.

21. A process for preparing ibuprofen, which comprises carbonylating a 1-(4'-isobutylphenyl)ethyl halide with carbon monoxide in an acidic medium containing water in an amount of about 1% to 600% based on the weight of the halide at a temperature in the range of about 10° C. to 225° C. and carbon monoxide pressure in the range of about 100 to 5,000 psig in the presence of (a) a palladium catalyst in which the palladium has a valence of 0–2 and (b) at least one ligand, which can tolerate conditions of reaction, complexed with the palladium.

22. A process of claim 21, wherein the 1-(4'-isobutylphenyl)ethyl halide is 1-(4'-isobutylphenyl)ethyl chloride.

23. A process of claim 21, wherein the 1-(4'-isobutylphenyl)ethyl halide is 1-(4'-isobutylphenyl)ethyl bromide.

24. A process of claim 21, wherein the palladium compound is selected from the group consisting of bis(triphenylphosphine)dichloro complex, bis(tributylphosphine) dichloro complex, bis(tricyclohexylphosphine)dichloro complex, piallyltriphenylphosphinedichloro complex, triphenylphosphinepiperidinedichloro complex, bis(cyclohexyloxime)dichloro complex, 1,5,9-cyclododecatrienedichloro complex, bis (triphenylphosphine)dicarbonyl complex, bis(triphenylphosphine)diacetate complex, bis(triphenylphosphine)dinitrate complex, bis(triphenylphosphine)sulfate complex, 2,4-pentanedione complex, tetrakis(triphenylphosphine) complex, and chlorocarbonylbis(triphenylphosphine) complex.

25. A process of claim 21, wherein the catalyst is palladium complexed with a phosphine ligand.

26. A process of claim 21, wherein the catalyst is selected from the group consisting of bis(triphenylphosphine)dichloro complex, bis(tributylphosphine)dichloro complex, bis(tricyclohexylphosphine)dichloro complex, piallyltriphenylphosphinedichloro complex, triphenylphosphinepiperidinedichloro complex, bis(triphenylphosphine) dicarbonyl complex, bis(triphenylphosphine)diacetate complex, bis(triphenylphosphine) dinitrate complex, bis(triphenylphosphine)sulfate complex, tetrakis(triphenylphosphine) complex, and chlorocarbonylbis(triphenylphosphine) complex.

27. A process of claim 26, wherein the catalyst is selected from the group consisting of bis(triphenylphosphine)dichloro complex, piallyltriphenylphosphinedichloro complex, triphenylphosphinepiperidinedichloro complex, bis(triphenylphosphine) dicarbonyl complex, bis(triphenylphosphine)diacetate complex, bis(triphenylphosphine) dinitrate complex, bis(triphenylphosphine)sulfate complex, tetrakis(triphenylphosphine) complex, and chlorocarbonylbis(triphenylphosphine) complex.

28. A process of claim 21, wherein the palladium compound is palladium bis(triphenylphosphine)dichloro complex.

29. A process of claim 21, wherein the catalyst is a palladium complex in an amount such that the mole ratio of palladium to the halide is in the range of about 1:25 to 1:20,000.

30. A process of claim 21, wherein the catalyst is a palladium complex in an amount such that the mole ratio of palladium to the halide is in the range of about 1:75 to 1:10,000.

31. A process of claim 21, wherein the catalyst is a palladium complex in an amount such that the mole ratio of palladium to the halide is in the range of about 1:100 to 1:6,000.

32. A process of claim 21, wherein the carbonylation is conducted in the presence of added hydrogen halide.

33. A process of claim 21, wherein the carbonylation is conducted in the presence of about 1% to 600% of water based on the weight of the halide initially present.

34. A process of claim 21, wherein the carbonylation is conducted in the presence of added hydrogen halide.

35. A process of claim 22, wherein the carbonylation is conducted in the presence added hydrogen halide.

36. A process of claim 35, wherein the hydrogen halide is hydrogen chloride.

37. A process of claim 35, wherein the hydrogen halide is hydrogen bromide.

38. A process of claim 35, wherein the amount of hydrogen halide added is the range of about 0.1 to 5 moles per mole of 1-(4'-isobutylphenyl)ethyl halide.

39. A process of claim 21, wherein the carbonylation is conducted in a solvent.

40. A process of claim 39, wherein the solvent is a ketone.

41. A process of claim 40, wherein the solvent is acetone.

42. A process of claim 40, wherein the solvent is methyl ethyl ketone.

43. A process of claim 21, wherein the temperature is in the range of 10° C. to 225° C.

44. A process of claim 21, wherein the temperature is in the range of 70° C. to 175° C.

45. A process of claim 21, wherein the carbon monoxide pressure is in the range of 100 to 5,000 psig.

46. A process of claim 21, wherein the carbon monoxide pressure is in the range of 600 to 3,000 psig.

47. A process of claim 24, wherein the palladium compound is palladium(II) chloride.

48. A process of claim 24, wherein the palladium compound is palladium(II) chloride, acetate, nitrate, or sulfate.

49. A process of claim 48, wherein the carbonylation is conducted in the presence of water and added hydrogen and halide ions.

50. A process of claim 22, wherein the carbonylation is conducted in the presence of an organic solvent.

51. A process of claim 49, wherein the hydrogen halide is added as dissociated hydrogen ions and halide ions.

52. A process of claim 43 wherein the temperature is gradually increased during the reaction.

53. A process for preparing ibuprofen, which comprises:
(A) charging a reactor with 1-chloro-1-(4-isobutylphenyl)ethane; and
(B) carbonylating the 1-chloro-1-(4-isobutylphenyl)ethane in the reactor with carbon monoxide in an acidic medium containing methyl ethyl ketone as a solvent and about 10% to 300% of water based on the weight of 1-chloro-1-(4-isobutylphenyl)ethane at a temperature in the range of about 10° C.–225° C. and a carbon monoxide pressure in the range of about 100–5,000 psig in the presence of (a) a palladium(II) compound and (b) at least one acid-stable monodentate phosphine ligand and in the presence of an amount of hydrogen chloride such as to provide an amount of about 0.1 to 5 mols of hydrogen chloride per mol of 1-chloro-1-(4-isobutylphenyl)ethane.

54. A process of claim 53, wherein the palladium(II) compound is palladium(II) chloride and the ligand is triphenylphosphine.

55. A process of claim 54, wherein the palladium and the ligand are present in amounts such as to provide about 100–6,000 mols of 1-chloro-1-(4-isobutylphenyl)ethane per mol of palladium complex and about 1–2 mols of ligand per mol of palladium.

56. A process of claim 55, wherein the hydrogen halide is added as dissociated hydrogen ions and halide ions.

57. A process for preparing ibuprofen, which comprises:
(A) charging a reactor with 1-chloro-1-(4-isobutylphenyl)-ethane; and
(B) carbonylating the 1-chloro-1-(4-isobutylphenyl)ethane in the reactor with carbon monoxide in an acidic medium containing methyl ethyl ketone as a solvent and about 10% to 300% of water based on the weight of 1-chloro-1-(4-isobutylphenyl)ethane and added hydrogen halide at a temperature in the range of about 10°–225° C. and a carbon monoxide pressure in the range of about 100–5,000 psig, in the presence of (a) a palladium(II) compound, and (b) at least one acid-stable monodentate phosphine ligand.

58. A process of claim 57, wherein the palladium(II) compound is palladium (II) chloride and the ligand is triphenylphosphine.

59. A process of claim 57, wherein the palladium and the ligand are present in amounts such as to provide about 100–6,000 mols of 1-chloro-1-(4-isobutylphenyl)ethane per mol of palladium and about 1–2 mols of ligand per mol of palladium.

60. A process for preparing ibuprofen from a corresponding halide substrate, which consists essentially of:
combining an initial reactant consisting of a 1-(4'-isobutylphenyl)ethyl halide with carbon monoxide in an acidic medium containing water, which is present in an amount of about 1% to 600% based on the weight of the halide initial reactant, in the presence of a palladium catalyst, wherein the mole ratio of palladium to 1-(4'-isobutylphenyl)ethyl halide is from about 1:25 to 1:20,000, and wherein said acidic aqueous medium further includes dissociated hydrogen ions and halide ions such that the molar ratios of dissociated hydrogen ions and halide ions to 1-(4'-isobutylphenyl)ethyl halide initial reactant are each about 0.1 to 5, at a temperature in the range of about 10° C. to 225° C., and a carbon monoxide pressure of about 100 to 5,000 psig, to form said ibuprofen; and
wherein said palladium catalyst includes (a) palladium having a valence of 0–2, and (b) at least one ligand, which can tolerate conditions of reaction and which is complexed with the palladium.

61. A process for preparing ibuprofen from a corresponding halide substrate, which consists essentially of:
charging a reactor with 1-(4'-isobutylphenyl)ethyl halide; and
carbonylating said halide with carbon monoxide;
wherein said carbonylation takes place in an acidic medium containing water, which is present in an amount of about 10% to 300% based on the weight of the halide charged, in the presence of a palladium catalyst, wherein the mole ratio of palladium to 1-(4'-isobutylphenyl)ethyl halide is from about 1:75 to 1:10,000, and wherein said acidic aqueous medium further includes dissociated hydrogen ions and halide ions such that the molar ratios of dissociated hydrogen ions and halide ions to 1-(4'-isobutylphenyl)ethyl halide charged are each about 0.2 to 2, at a temperature in the range of about 70° C. to 175° C. and a carbon monoxide pressure of about 600 to 3,000 psig, to form said ibuprofen; and wherein said palladium catalyst includes (a) palladium having a valence of 0–2, and (b) at least one ligand, which can tolerate conditions of reaction and which is complexed with the palladium.

62. A process for preparing ibuprofen from a corresponding halide substrate, which consists essentially of:

charging a reactor with a 1-(4'-isobutylphenyl)ethyl halide; and carbonylating said halide with carbon monoxide;

wherein said carbonylation takes place in an acidic medium containing methyl ethyl ketone and water, which is present in an amount of about 10% to 300% based on the weight of the halide charged, in the presence of a palladium catalyst, wherein the mole ratio of palladium to 1-(4'-isobutylphenyl)ethyl halide is from about 1:100 to 1:6,000, and wherein said acidic aqueous medium further includes dissociated hydrogen ions and chloride ions such that the molar ratios of dissociated hydrogen ions and chloride ions to 1-(4'-isobutylphenyl)ethyl halide charged are each about 0.2 to 2.0, at a temperature in the range of about 70° C. to 175° C., and a carbon monoxide pressure of about 600 to 3,000 psig, to form said ibuprofen; and wherein said palladium catalyst includes (a) palladium having a valence of 0–2, and (b) at least one ligand, which can tolerate conditions of reaction and which is complexed with the palladium.

63. A process for preparing ibuprofen from an ibuprofen substrate, which consists essentially of:

charging a reactor with said ibuprofen substrate, wherein said ibuprofen substrate consists of 1-(4'-isobutylphenyl)ethyl chloride; and carbonylating said substrate with carbon monoxide;

wherein said carbonylation takes place in an acidic medium containing water, which is present in an amount of about 10% to 300% based on the weight of the chloride charged, in the presence of a palladium catalyst, wherein the mole ratio of palladium to 1-(4'-isobutylphenyl)ethyl chloride is from about 1:100 to 1:6,000, and wherein said acidic aqueous medium further includes dissociated hydrogen ions and chloride ions such that the molar ratios of dissociated hydrogen ions and chloride ions to 1-(4'-isobutylphenyl)ethyl chloride charged are each about 0.2 to 2, at a temperature in the range of about 70° C. to 175° C., and a carbon monoxide pressure of about 600 to 3,000 psig, to form said ibuprofen; and wherein said palladium catalyst includes (a) palladium having a valence of 0–2, and (b) at least one ligand, which can tolerate conditions of reaction and which is complexed with the palladium.

64. The process of claim 63, wherein the palladium catalyst is selected from the group consisting of palladium bis(triphenylphosphine)dichloro complex, palladium bis (tributylphosphine)dichloro complex, palladium bis (tricyclohexylphosphine)dichloro complex, palladium piallyltriphenylphosphinedichloro complex, palladium triphenylphosphinepiperidinedichloro complex, palladium bis(cyclohexyloxime)dichloro complex, palladium 1,5,9-cyclododecatrienedichloro complex, palladium bis (triphenylphosphine)dicarbonyl complex, palladium bis (triphenylphosphine)diacetate complex, palladium bis (triphenylphosphine)dinitrate complex, palladium bis (triphenylphosphine)sulfate complex, palladium 2,4-pentanedione complex, palladium tetrakis (triphenylphosphine) complex, and palladium chlorocarbonylbis(triphenylphosphine) complex.

65. The process of claim 64, wherein the carbonylation reaction is carried out in the presence of an organic solvent selected from the group consisting of methyl ethyl ketone, acetone, 2-pentanone, 3-pentanone, acetophenone, benzene, toluene, tetrahydrofuran, and dioxane, and wherein the solvent is present in a weight ratio of solvent to the 1-(4'-isobutylphenyl)ethyl chloride of from about 0 to 10:1.

66. A process for preparing naproxen, which comprises:

(A) charging a reactor with 1-(6'-methoxy-2'-napthyl) ethyl chloride; and (B) carbonylating the 1-(6'-methoxy-2'-napthyl)ethyl chloride in the reactor with carbon monoxide in an acidic medium containing methyl ethyl ketone as a solvent and about 10% to 300% of water based on the weight of 1-(6'-methoxy-2'-napthyl)ethyl chloride at a temperature in the range of about 10° C.–225° C. and a carbon monoxide pressure in the range of about 100–5,000 psig in the presence of (a) a palladium(II) compound and (b) at least one acid-stable monodentate phosphine ligand and in the presence of an amount of hydrogen chloride such as to provide an amount of about 0.1 to 5 mols of hydrogen chloride per mol of 1-(6'-methoxy-2'-napthyl)ethyl chloride.

67. A process for preparing naproxen, which comprises:

(A) charging a reactor with 1-(6'-methoxy-2'-napthyl) ethyl chloride; and (B) carbonylating the 1-(6'-methoxy-2'-napthyl)ethyl chloride in the reactor with carbon monoxide in an acidic medium containing methyl ethyl ketone as a solvent and about 10% to 300% of water based on the weight of 1-(6'-methoxy-2'-napthyl)ethyl chloride and added hydrogen halide at a temperature in the range of about 10°–225° C. and a carbon monoxide pressure in the range of about 100–5,000 psig, in the presence of (a) a palladium(II) compound, and (b) at least one acid-stable monodentate phosphine ligand.

68. A process for preparing naproxen from a corresponding halide substrate, which consists essentially of:

combining an initial reactant consisting of a 1-(6'-methoxy-2'-napthyl)ethyl halide with carbon monoxide in an acidic medium containing water, which is present in an amount of about 1% to 600% based on the weight of the halide initial reactant, in the presence of a palladium catalyst, wherein the mole ratio of palladium to 1-(6'-methoxy-2'-napthyl)ethyl halide is from about 1:25 to 1:20,000, and wherein said acidic aqueous medium further includes dissociated hydrogen ions and halide ions such that the molar ratios of dissociated hydrogen ions and halide ions to 1-(6'-methoxy-2'-napthyl)ethyl halide initial reactant are each about 0.1 to 5, at a temperature in the range of about 10° C. to 225° C., and a carbon monoxide pressure of about 100 to 5,000 psig, to form said naproxen; and wherein said palladium catalyst includes (a) palladium having a valence of 0–2, and (b) at least one ligand, which can tolerate conditions of reaction and which is complexed with the palladium.

69. A process for preparing naproxen from a corresponding halide substrate, which consists essentially of:

charging a reactor with 1-(6'-methoxy-2'-napthyl)ethyl halide; and carbonylating said halide with carbon monoxide;

wherein the carbonylation takes place in an acidic medium containing water, which is present in an amount of about 10% to 300% based on the weight of the halide charged, in the presence of a palladium catalyst, wherein the mole ratio of palladium to 1-(6'-methoxy-2'-napthyl)ethyl halide is from about 1:75 to 1:10,000, and wherein said acidic aqueous medium further includes dissociated hydrogen ions and halide ions such that the molar ratios of dissociated hydrogen ions and halide ions to 1-(6'-methoxy-2'-napthyl)ethyl halide charged are each about 0.2 to 2, at a temperature in the range of about 70° C. to 175° C. and a carbon monoxide pressure of about 600 to 3,000 psig, to form said naproxen; and wherein said palladium catalyst includes (a) palladium having a valence of 0–2, and (b) at least one ligand, which can tolerate conditions of reaction and which is complexed with the palladium.

70. A process for preparing naproxen from a corresponding halide substrate, which consists essentially of:

charging a reactor with 1-(6'-methoxy-2'-napthyl)ethyl halide; and carbonylating said halide with carbon monoxide;

wherein the carbonylation takes place in an acidic medium containing methyl ethyl ketone and water, which is present in an amount of about 10% to 300% based on the weight of the halide charged, in the presence of a palladium catalyst, wherein the mole ratio of palladium to 1-(6'-methoxy-2'-napthyl)ethyl halide is from about 1:100 to 1:6,000, and wherein said acidic aqueous medium further includes dissociated hydrogen ions and chloride ions such that the molar ratios of dissociated hydrogen ions and chloride ions to 1-(6'-methoxy-2'-napthyl)ethyl halide charged are each about 0.2 to 2.0, at a temperature in the range of about 70° C. to 175° C., and a carbon monoxide pressure of about 600 to 3,000 psig, to form said naproxen; and wherein said palladium catalyst includes (a) palladium having a valence of 0–2, and (b) at least one ligand, which can tolerate conditions of reaction and which is complexed with the palladium.

71. A process for preparing naproxen from a naproxen substrate, which consists essentially of:

charging a reactor with said naproxen substrate, wherein said naproxen substrate consists of 1-(6'-methoxy-2'-napthyl)ethyl chloride; and carbonylating said substrate with carbon monoxide;

wherein the carbonylation takes place in an acidic medium containing water, which is present in an amount of about 10% to 300% based on the weight of the chloride charged, in the presence of a palladium catalyst, wherein the mole ratio of palladium to 1-(6'-methoxy-2'-napthyl)ethyl chloride is from about 1:100 to 1:6,000, and wherein said acidic aqueous medium further includes dissociated hydrogen ions and chloride ions such that the molar ratios of dissociated hydrogen ions and chloride ions to 1-(6'-methoxy-2'-napthyl) ethyl chloride charged are each about 0.2 to 2, at a temperature in the range of about 70° C. to 175° C., and a carbon monoxide pressure of about 600 to 3,000 psig, to form said naproxen; and wherein said palladium catalyst includes (a) palladium having a valence of 0–2, and (b) at least one ligand, which can tolerate conditions of reaction and which is complexed with the palladium.

\* \* \* \* \*